United States Patent [19]

Georgiev et al.

[11] 4,290,971
[45] Sep. 22, 1981

[54] METHOD OF PREPARING 2-(PHENYLAMINO)-IMIDAZOLINES-(2)

[75] Inventors: Atanas G. Georgiev; Kino D. Andreev; Kina V. Konstantinova, all of Sofia, Bulgaria

[73] Assignee: DSO "Pharmachim", Sofia, Bulgaria

[21] Appl. No.: 110,608

[22] Filed: Jan. 9, 1980

Related U.S. Application Data

[63] Continuation-in-part of Ser. No. 4,982, Jan. 19, 1979, abandoned, and a continuation-in-part of Ser. No. 4,984, Jan. 19, 1979, abandoned.

[51] Int. Cl.$^3$ ............................................. C07C 157/14
[52] U.S. Cl. ................................. 260/453.5; 548/315
[58] Field of Search ............ 260/558 S, 558 R, 562 R, 260/562 P, 564 E, 453.5, 453.4

[56] References Cited

U.S. PATENT DOCUMENTS 4,021,571 5/1977 Kolling et al. ................. 260/453.5
4,066,695 1/1978 Cohen et al. ................... 260/453.5

FOREIGN PATENT DOCUMENTS 2608488 9/1976 Fed. Rep. of Germany .

OTHER PUBLICATIONS

Neidleim et al., Chem. Abst. 1975, vol. 83, No. 58372c.
Kristian et al., Chem. Abst. 1979, vol. 91, No. 123665d.

*Primary Examiner*—Henry R. Jiles
*Assistant Examiner*—Natalia Harkaway
*Attorney, Agent, or Firm*—Karl F. Ross

[57] ABSTRACT

A process for preparing compounds of the formula:

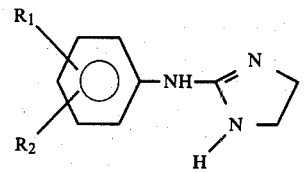

or pharmaceutically acceptable salts thereof, wherein $R_1$ and $R_2$ each individually are hydrogen, halogen, or nitro, which comprises the steps of: (a) alkylating a compound of the formula:

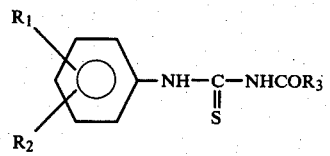

wherein $R_3$ is $C_1$ to $C_4$ alkyl or phenyl, with a compound of the formula:

$$R_4-X$$

wherein $R_4$ is $C_1$ to $C_6$ alkyl or phenyl-alkyl where the alkyl is $C_1$ to $C_4$ and X is halogen, in the presence of a base to yield a compound of the formula:

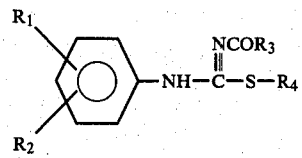

and; (b) cyclizing the compound formed during step (a) with ethylenediamine mono-p-toluenesulphonate at a temperature of 100° to 200° C. to yield the desired product. New intermediate compounds are also disclosed. The desired products have antihypertensive properties.

2 Claims, No Drawings

METHOD OF PREPARING 2-(PHENYLAMINO)-IMIDAZOLINES-(2)

CROSS REFERENCE TO RELATED APPLICATIONS

This application is a continuation-in-part of copending Ser. No. 004,982 filed Jan. 19, 1979, now abandoned, and of Ser. No. 004,984 filed Jan. 19, 1979, now abandoned.

FIELD OF THE INVENTION

The invention relates to a method of preparing 2-(phenylamino)-imidazolines-(2) or pharmaceutically acceptable salts thereof. The invention further relates to new intermediate compounds formed during the preparation of the 2-(phenylamino)-imidazolines-(2) or pharmaceutically acceptable salts thereof.

BACKGROUND OF THE INVENTION

It is well known in the art that compounds of the formula:
imidazolinyl)-phosphinechloride according to Bulgarian Pat. Nos. 12,391 and 12,394, or with 1-acylimindazoline-2-one according to Bulgarian Patent Application No. 26,251. There are other variants of the above-mentioned known methods.

A disadvantage of the known methods is the unsatisfactory yield. In other cases a disadvantage appears to be the unstable intermediates which are difficult to purify, for example the cyanamides. Other weak points of the known methods are also the difficulties accompanying the isolation and the purification of 2-(phenylamino)-imidazolines-(2).

As stated hereinabove the invention also relates to new intermediate compounds used in the production of the 2-(phenylamino)-imidazolines. These intermediate compounds are N-phenyl-N'-acyl-S-alkylisothioureas.

There are familiar N-phenyl-N'-acylthioureas, for example from the publications of J. Douglas, F. Dains, J. Am. Chem. Soc. 56, 1408 (1934); R. Frank, P. Smith, Org. Synth. Coll. Vol. 3, New York, p. 736(1955), publications of At. Georgiev, K. Mondeshka and K. Andreev, Collection of Works from NIHFI, vol. 7, Sofia, wherein $R_4$ is $C_1$ to $C_6$ alkyl or phenyl-alkyl wherein the alkyl is $C_1$ to $C_4$, and X is halogen (e.g. F, Cl, Br, or I). The alkylation is carried out in a presence of a base. Preferable bases include alkali metal carbonates (e.g. $Na_2CO_3$, $K_2CO_3$) and alkali metal hydroxides (e.g. NaOH, KOH). In addition to alkali metal carbonates any alkali metal salt of a weak acid may be employed as a base.

The reaction is carried out preferably in a polar organic solvent such as a lower aliphatic alcohol (e.g. methanol or ethanol) or a lower aliphatic ketone (e.g. acetone, methyl-ethyl-ketone). Preferably the alkylation is carried out at a temperature of 40° to 150° C. Preferably also there is a slight molar excess of the compound of formula III and the base in terms of the compound of formula II.

After the alkylation is completed compounds of the formula IV are produced:

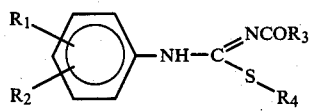

The compounds of the formula IV then undergo a cyclization reaction with ethylenediamine mono-p-toluenesulphonate in a molar ratio that is preferably at least 1:1 and more preferably at least 2:1 at a temperature of 100° to 200° C., to produce compounds of formula I.

The process can be further illustrated according to the following reaction scheme:

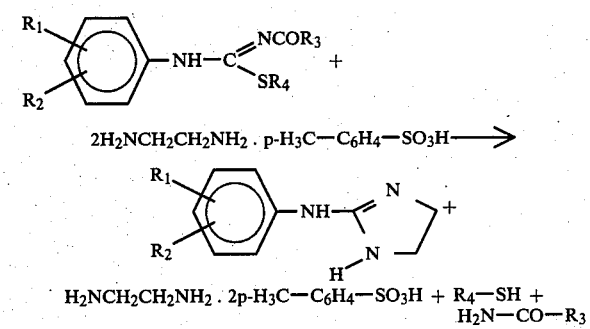

Preferably the cyclization is carried out in an alcohol medium or in a mixture of alcohols. The alcohols preferably contain 5 to 8 carbon atoms (e.g. amyl alcohol, cyclohexanol) and boil in the range of 100° to 200° C. after heating for several hours. Preferably the range is 130° to 180° C.

Applicants also wish to emphasize that the new intermediate compounds of formula IV are themselves part of the invention. These intermediates were produced from readily available starting materials and can be obtained in pure form without much difficulty. The fact that the intermediates can be obtained in highly pure form aids in the production of the products of formula I in highly purified form.

Applicants also mention that the acid addition salts which are pharmaceutically acceptable may be formed of the compounds of formula I. Preferably the pharmaceutically acceptable salt is a hydrohalide, preferably the hydrochloride.

According to the invention, the synthesis of 2-(phenylamino)-imidazolines-(2) is achieved by a new and a very simple method, thanks to the new type of reaction. On the basis of the known processes to obtain imidazoline derivatives by means of cyclization of N-phenyl-S-alkylisothiuronium salts with ethylenediamine or ethylenediamine mono-p-toluenesulphonate, and elimination of alkylmercaptane and ammonia, it was almost impossible to expect the possibility of cyclization of N-phenyl-N'-acyl-S-alkylisothioureas under the action of ethylenediamine mono-p-toluolsulphonate, since at first sight the carrying out of the process with elimination of large size molecules, as for example the acid amides - acetamide, benzamide and others, seemed almost impossible, although actually is has been done.

An advantage of the new method of synthesis of substituted 2-(phenylamino)-imidazolines-(2) by the respective N-phenyl-N'-acyl-S-alkylisothioureas, is the shorter and safer synthetic method compared to the synthetic method where other starting products are used for the same purpose, e.g. N-(phenyl-S-alkylisothiuronium salts or phenylcyanamides.

The advantage of the new process is especially apparent where compared to the prior art synthesis of 2-(2',6'-dichlorophenylamino)imidazoline by reaction of ethylenediamine or ethylene-mono-p-toluenesulphonate and 2,6-dichlorophenyl-S-methylisothiuronium salt or 2,6-dichlorophenylcyanamide. In each case the prior art processes cannot lead from N-phenyl-N'-acylisothioureas, the starting material, to the compounds of Formula I in less than three steps. By comparison the compound of Formula II according to the instant invention, can be converted to a compound of Formula I in two stages.

The following examples clarify the invention in detail:

EXAMPLE 1

N-(2,6-dichlorophenyl)-N'-acetyl-S-methyl-isothiourea 26.3 g (0.1M) of N-(2,6-dichlorophenyl)-N'-acetylthiourea, 9.9 g (0.06M) of ground 2 $K_2CO_3.3 H_2O$, 8.3 ml (0.13M) of methyliodide and 200 ml of acetone are put to boil and are energetically shaken for 5 hours. The acetone is distilled off and the residue is washed with water and filtered. The sediment on the filter is washed once or twice more with water. After drying the product is boiled in a reflux with isopropanol 1:6, weight:volume) and is filtered. From the filtrate 22.0 g of N-(2,6-dichloro-phenyl)-N'-acetyl-S-methylisothiourea (79.4% of the theoretical yield), melting point 137° to 140° C. are isolated.

Elemental analysis of $C_{10}H_{10}Cl_2N_2OS$ (M=277.14); Calculated: C % 43.33; H % 3.63; Cl % 25.56; N % 10.10; S % 11.57; Found: C % 43.55; H % 3.85; Cl % 25.41; N % 9.80; S % 11.22.

EXAMPLE 2

N-(2,6-dichlorophenyl)-N'-acetyl-S-methylisothiourea.

13.15 g (0.05 M) of N-(2,6-dichlorophenyl)-N'-acetylthiourea, 4.95 g (0.03 M) of ground 2 $K_2CO_3 . 3 H_2O$, 3.9 ml (0.06 M) of methyliodide and 100 ml of ethyl alcohol are boiled in a reflux and shaken for 5 hours. After the solvent is distilled off, the reaction mixture remaining in the flask is washed with water and filtered. The sediment on the filter is washed several times with water and then is dried.

After recrystallization from ethyl alcohol are obtained 5.05 g (31.2% of the theoretical yield) N-(2,6- dichlorophenyl). N'-acetyl-S-methylisothiourea with a melting point 134°–139°.

EXAMPLE 3

N-(2,6-dichlorophenyl)-N'-acetyl-S-methylisothiourea.

5.2 g (0.02 M) of N-(2,6-dichlorophenyl)-N'-acetyl-thiourea, 1.3 g (0.012 M) of sodium carbonate, 1.5 ml (0.024 M) of methyliodide and 200 ml of acetone are boiled under energetic shaking for 10 hours. The acetone is distilled off and the residue is washed and then filtered. After drying 4.9 g (88.5% from the theoretical yield of N-(2,6-dichlorophenyl)-N'-acetyl-S-methylisothiourea are obtained with a melting point 135–139° C. After recrystallization from ethanol, the melting point of the product is 139°–141° C.

Example 4

N-(2,6-dichlorophenyl)-N'-acetyl-S-methylisothiourea 26.3 g (0.1 M) of N-(2,6-dichlorophenyl)-N'-acetyl-thiourea, 8.1 g (0.12 M as 100%) of potassium hydroxide, 7.7 ml (0.12 M) of methyliodide and 250 ml of ethanol are mixed and are heated in a water bath at 50°–60° for 5 hours. The ethanol is distilled off. The residue in the flask is washed with water and filtered. After recrystallization from isopropanol 14.0 g (50.5 % of the theoretical yield) of N-(2,6-dichlorophenyl)-N'-acetyl-S-methylisothiourea are isolated.

EXAMPLE 5

N-(2,6-dichlorophenyl)-N'-acetyl-S-methylisothiourea 26.3 g (0.1 M) of N-(2,6-dichlorophenyl)-N'-acetyl-thiourea, 6.4 g (0.06 M) of sodium carbonate, 8 ml (0.123 M) of methyliodide and 200 ml of ethanol are mixed and heated for 4 hours in a water bath at 70°–75°. The ethanol is distilled off. The residue is washed with water and filtered. The sediment, after drying, is boiled with 180 ml of iso-propanol and then is filtered. From the filtrate 15.3 g (55.2% of the theoretical yield) of N-(2,6-dichlorophenyl)-N'-acetyl-S-methylisothiourea with a melting point of 137°–141° are isolated.

EXAMPLE 6

N-(2,6-dichlorophenyl)-N'-acetyl-S-ethylisothiourea 7.9 g (0.03 M) of N-(2,6-dichlorophenyl)-N'-acetyl-thiourea, 3.0 g (0.022 M) of ground potassium carbonate, 3.0 ml (0.04 M) of ethyliodide and 100 ml of acetone are mixed and then boiled for 5 hours. The acetone then is distilled off. The residue is washed with water and filtered. 6.8 g (80.5 % of the theoretical yield) of N-(2,6-dichlorophenyl)-N'-acetyl-S-ethylisothiourea with a melting point of 97°–100° are obtained. After recrystallization from ethyl alcohol the product has a melting point of 99°–102° C. The yield is 56 % of the theoretical one.

Elemental analysis of $C_{11}H_{12}Cl_2N_2OS$: (M=291.16); Calculated: C% 45.37; H% 4.15; Cl% 24.38; N% 9.62; S% 11.01; Found: 45.80; 4.45; 23.92; 9.60; 10.80.

EXAMPLE 7

N-(2,6-dichlorophenyl)-N'-benzoyl-S-methylisothiourea 19.5 g (0.06 M) of N-(2,6-dichlorophenyl)-N'-benzoyl thiourea, 5.5 g (0.04 M) of ground potassium carbonate, 5.1 ml (0.08 M) of methyliodide and 200 ml of acetone are boiled in a reflux for 4 hours under energetic shaking. The acetone is distilled off. 200 ml of water are added to the residue and it is then filtered. The sediment on the filter is washed to a neutral pH. After drying 20.2 g (99% of the theoretical yield) of N-(2,6-dichlorophenyl)-N'-benzoyl-S-methylisothiourea are obtained with melting point 127–129° C. This product being recrystallized from ethyl alcohol gives the corresponding isothiourea with a melting point of 128°–130° C. and 85% yield of the theoretical one.

Elemental analysis of $C_{15}H_{12}Cl_2N_2OS$: (M=339.20); Calculated: C% 53.11; H% 3.56; Cl% 20.90; N% 8.25; S% 9.45; Found: 53.50; 3.35; 21.29; 7.95; 9.32.

EXAMPLE 8

N-(2,6-dichlorophenyl)-N'-propionyl-S-methyl-isothiourea 33.2 g (0.12 M) of N-(2,6-dichlorophenyl)-N'-propionyl-thiourea, 10.5 g (0.08 M) of ground potassium carbonate, 9.6 ml (0.15 M) of methyliodide and 300 ml of acetone are boiled in a reflux for 4 hours under energetic shaking. The acetone is distilled off, 300 ml of water are added to the residue. The sediment is filtered and dried. 34.4 g (98.5% of the theoretical yield) of N-(2,6-dichlorophenyl)-N'-propionyl-S-methyl-isothiourea with a melting point of 165°–170° are obtained. After recrystallization from ethyl alcohol 23.5 g of the product (68.2 % from the raw one) are obtained with a melting range of 173°–176°.

Elemental analysis of $C_{11}H_{12}Cl_2N_2OS$: (M=291.16); Calculated: C% 45.37; H% 4.15; Cl% 24.38; N% 9.62; S% 11.01; Found: 45.80; 4.50; 24.18; 9.59; 11.28.

EXAMPLE 9

N-(2,6-dichlorophenyl)-N'-acetyl-S-benzyl-isothiourea 5.2 g (0.02 M) of N-(2,6-dichlorophenyl)-N'-acetyl-thiourea, 1.7 g of (0.012 M) of ground potassium carbonate 2.6 ml (0.024 M) of benzylchloride and 80 ml of acetone are boiled in a reflux being energetically shaken for 4 hours. The acetone is distilled off. The product in the flask is washed with water and is filtered. After drying N-(2,6-dichlorophenyl)-N'-acetyl-S-benzylisothiourea is obtained with a melting point of 84°–95° C. After being recrystallized twice from ethanol it has a melting point of 99°–101° C., whereby 1.7 g are isolated (24% of the theoretical yield).

Elemental analysis of $C_{16}H_{14}Cl_2N_2OS$: (M=353.23); Calculated: C% 54.43; H% 3.99; Cl% 20.06 N% 7.93; S% 9.07; Found: 54.85; 4.25; 19.64; 7.86; 9.10.

EXAMPLE 10

N-(2,6-dichlorophenyl)-N'-acetyl-S-n-butylisothiourea 5.2 g (0.02 M) of N-(2,6-dichlorophenyl)-N'-acetyl-thiourea, 2.1 ml (0.015 M) of ground potassium carbonate, 3.2 ml (0.03 M) of n-butylbromide and 50 ml of acetone are boiled in a reflux under energetic shaking for 4 hours. The acetone is distilled off. The residue in the flask is washed with water and filtered. 5.8 g (90.6% of the theoretical yield) of N-(2,6-dichlorophenyl)-N'-acetyl-S-n-butylisothiourea with a melting point of 84°–89° are obtained. After recrystallization from ethanol the product has a melting point of 97°–100°.

Elemental analysis of $C_{13}H_{16}Cl_2N_2O S$: (M=319.21); Calculated: C% 48.91; H% 5.04; Cl% 22.21; N% 8.77; S% 10.04; Found: 49.30; 4.90; 22.43; 8.45; 9.60.

EXAMPLE 10a

N-(2,6-dichlorophenyl)-N'-acetyl-S-isobutyl-isothiourea 5.2 g (0.02 M) of N-(2,6-dichlorophenyl)-N'-acetyl-thiourea, 2.1 g (0.015M) of ground potassium carbonate, 3.3 ml (0.03M) of isobutylbromide and 50 ml of acetone were heated together under stirring and reflux for 4 hours. The acetone was then distilled off. The residue in the flask was washed with water and then filtered. 5.9 g (92% of theoretical yield) of N-(2,6-dichlorophenyl)-N'-acetyl-S-isobutyl-thiourea melting at 106° to 112° were obtained. After recrystallization from benzene the product melted at 114° to 116° C.

Elemental analysis of $C_{13}H_{16}Cl_2N_2OS$: (M=319.21); Calculated: C% 48.91; H% 5.04; Cl% 22.21; N% 8.77; S% 10.04; Found: 48.90; 5.29; 22.65; 8.90; 9.76.

EXAMPLE 11

N-(2,5-dichlorophenyl)-N'-acetyl-S-methyl-isothiourea 26.3 g (0.1 M) of N-(2,5-dichlorophenyl)-N'-acetyl-thiourea, 8.3 g (0.06 M) of ground potassium carbonate, 7.5 ml (0.12 M) of methyliodide and 300 ml of acetone are refluxed under mixing for four hours. The acetone is distilled off. Water is added to the residue in the flask, it is mixed and filtered. After drying 21.4 g (77.3 % from the theoretical yield) of N-(2,5-dichlorophenyl)-N'-acetyl-S-methylisothiourea are obtained with a melting point of 107°-123° C. After recrystallization from isopropanol a product is obtained with 63.3% yield of the theoretical product and melting at a temperature of 109°-111° C.

Elemental analysis of $C_{10}H_{10}Cl_2N_2O$ S; M=277.14; Calculated: C% 43.33; H% 3.63; Cl% 25.56; N% 10.10; S% 11.57; Found: 43.80; 3.60; 25.90; 9.96; 11.10.

EXAMPLE 12

N-(3-iodophenyl)-N'-acetyl-S-methylisothiourea 19.1 g (0.05 M) of N-(3-iodophenyl)-N'-acetylthiourea, 4.2 g (0.03 M) of potassium carbonate, 3.8 ml (0.06 M) of methyliodide and 100 ml of acetone are boiled during 4 hours. The acetone is distilled off. Water is added to the residue, it is heated up to 50°-60° and is ground. The sediment is filtered. After drying 19.8 g (100% of the theoretical yield) of N-(3-iodophenyl)-N'-acetyl-S-methylisothiourea are obtained with a melting point of 80°-90° C. After being twice recrystallized from ethanol and isopropanol, 9.9 g (50% of the raw product) of N-(3-iodophenyl)-N'-acetyl-S-methylisothiourea are obtained with a melting point of 92°-93°.

Elemental analysis of $C_{15}H_{13}J\ N_2O\ S$: M=396.06; Calculated: C% 45.45; H% 3.30; J% 32.05; N% 7.07; Found: 45.20; 3.80; 31.74; 7.18.

Example 13

N-(O-fluorophenyl)-N'-benzoyl-S-ethylisothiourea 27.4 (0.1 M) of N-(o-fluorophenyl)-N'-benzoyl-thiourea, 16.6 g (0.12 M) of potassium carbonate, 10 ml (0.12 m) of ethyliodide and 200 ml of ethylmethylketone are boiled in a reflux for four hours.

The solvent is distilled off. The residue is washed with water and then filtered. After drying 30 g (99.3% of the theoretical yield) of N-(o-fluorophenyl)-N'-benzoyl-S-ethylisothiourea with a melting point of 95°-97° are obtained.

After recrystallization twice from ethyl alcohol and ethylacetate 19.4 g of (64% of the theoretical yield) the product with a 99°-101° melting point are obtained.

Elemental analysis of $C_{16}H_{15}F\ N_2O\ S$: M=302.34; Calculated: C% 63.56; H% 5.00; N% 9.26; S% 10.60; Found: 63.00; 5.24; 9.47; 10.57.

EXAMPLE 14

N-phenyl-N'-benzoyl-S-methylisothiourea 12.8 g (0.05 M) of N-phenyl-N'-benzoyl-thiourea, 5.3 g (0.038M) of potassium carbonate, 4.7 ml (0.075 M) of methyliodide and 200 ml of acetone are boiled in a reflux and constantly mixed for five hours. After cooling the sediment is filtered. The filtrate is washed with 150 ml of water. The separated sediment is ground and filtered. 12.4 g (93.3% of the theoretical yield) of N-phenyl-N'-benzoyl-S-methylisothiourea with a melting point of 78°-94° are obtained. After recrystallization twice from ethanol and ethylacetate 7.4 g (54.8 % of the raw one) of product with a melting temperature of 102°-104° C. are obtained.

Elemental analysis of $C_{15}H_{14}N_2OS$: (M=270.32); Calculated: C% 66.65; H% 5.21; N% 10.35; S% 11.85; Found: 66.70; 5.35; 10.65; 11.56.

EXAMPLE 15

N-(o-nitrophenyl)-N'-acetyl-S-methylisothiourea 6.5 g (0.026 M) of N-(o-nitrophenyl)-N'-acetyl-thiourea, 2.1 g (0.015 M) of potassium carbonate, 1.9 ml (0°-0.29 M) of methyl iodide and 70 ml of acetone are boiled in a reflux for four hours. The acetone is distilled off. Water is added to the residue and it is filtered. After drying 6.6 g (100% of the theoretical yield) of the product are obtained with a melting point of 118°-160°. After recrystallization twice from ethanol and isopropanol N-(o-nitrophenyl)-N'-acetyl-S-methylisothiourea with a melting point of 120°-122° C. and 42% yield of the theoretical one is obtained.

Elemental analysis of $C_{10}H_{11}N_3O_3S$: M=(253.25); Calculated: C% 47.42; H% 4.38; N% 16.59; S% 12.66; Found: 47.85; 4.75; 16.35; 12.56.

EXAMPLE 16

2-(2',6'-dichlorophenylamino)-imidazoline-(2)-hydrochloride.

27.7 g (0.1 M) of N-(2,6-dichlorophenyl)-N'-acetyl-S-methylisothiourea and 76.6 g (0.33 M) of ethylenediamine mono-p-toluenesulphonate are heated in 280 ml of iso-amyl alcohol under boiling in a reflux for twenty hours. The sediment of ethylenediamine mono- and di-p-toluenesulfphonates after one night is separated by means of filtration. The filtrate is put under vacuum distillation until an oily residue is obtained. A solution of 12.7 g of sodium carbonate in 140 ml of water is added to the residue and is mixed for one hour. After one night the separated sediment is filtered and twice washed with sodium carbonate solution and then with water. The product is dried. 17.1 g (74.4% of the theoretical yield) of 2-(2',6'-dichlorophenylamino)-imidazoline-(2) with a melting point of 134°-139° C. are obtained.

To 17.1 g of the obtained base are added 75 ml of water, 7.5 ml of concentrated hydrochloric acid, and 2 g of active charcoal. The reaction mixture is heated in a water bath and then filtered. From the water filtrate are obtained 12.4 g (62.6 % from the base) pure, very small crystalline 2-(2',6'-dichlorophenylamino)-imidazoline (2) hydrochloride with a melting point of 303–306° C. (with decomposition).*

*Melting point °C. of
2-(2',6'-dichlorophenylamino)-imidazoline-(2) hydrochloride

| According to | | |
|---|---|---|
| | Belg. Pat. 623305 | 305 |
| | Belg. Pat. 653933 | 308–310 |
| | Brit. Pat. 1034938 | 311–315 |
| | DDR Pat. 68509 | 305–310 decom. |
| Bulg. Pat. | | |
| | Appln. 26251 | 304–310 decom. |

The alkalized water filtrates are regenerated and 3.3 g of the base product are recovered, purified and converted into the hydrochloride salt. Combined are obtained 13.7 g of 2-(2',6'-dichlorophenylamino)-imidazoline-(2) hydrochloride or 51.6% of the theoretical yield.

EXAMPLE 17

2-(2',6'-dichlorophenylamino)-imidazoline-(2)-hydrochloride 2.8 g (0.01 M) of N-(2,6-dichlorophenyl)-N'-acetyl-S-methylisothiourea and 7.0 g (0.03 M) of ethylenediamine mono-p-toluenesulphonate are boiled in a reflux in 20 ml of benzyl alcohol. The reaction mixture is washed with 20 ml of a saturated water solution of sodium carbonate. The two layers separate from one another in a funnel and the alcohol layer is washed twice with 20 ml of water thereafter it is dried with anhydrous sodium sulphate. From the dried solution with a solution of hydrochloric acid in ethylacetate 1.55 g (58.2% of the theoretical yield) of 2-(2',6'-dichlorophenylamino)-imidazoline-(2) hydrochloride with a melting point of 303°–306° C. are precipitated.

EXAMPLE 18

2-(2',6'-dichlorophenylamino)-imidazoline-(2)

2.8 g (0.01 M) of N-(2,6-dichlorophenyl)-N'-acetyl-S-methylisothiourea and 7.0 g (0.03 M) of ethylenediamine mono-p-toluenesulphonate are heated in 25 ml of cyclohexanol under boiling for 5 hours. The solvent is removed under vacuum. The residue is mixed with an aqueous solution of sodium carbonate. The separated oily product is dissolved in ethylacetate and is precipitated with a solution of hydrochloric acid in ethylacetate. The sediment is filtered and washed with acetone. 1.3 g of 2-(2',6'-dichlorophenylamino)-imidazoline-(2) hydrochloride are obtained, and it is dissolved in water and the water solution is then alkalized with a saturated aqueous solution of sodium carbonate. The separated basic product is filtered and then dried. 0.8 g of 2-(2',6'-dichlorophenylamino)-imidazoline-(2) with a melting point of 138°–142° C. are obtained.*
The yield is 35% of the theoretical one.

*Melt. point °C. of
2-(2',6'-dichlorophenylamino)-imidazoline-(2).

| According to | Belg. Patent 623305 | 130 |
|---|---|---|
| | Belg. Patent 653988 | 137–138 |
| | Brit. Patent 1034988 | 137–138 |
| | DDR Patent 68509 | 141–143 |
| | DDR 68510 | 138–142 |
| | Bulg. Pat. Appln. 26251 | 143–146 |

EXAMPLE 19

2-(2',6'-dichlorophenylamino)-imidazoline-(2)

2.9 g (0.01 M) of N-(2,6-dichlorophenyl)-N'-acetyl-S-ethyl-isothiourea and 7.0 g (0.03 M) of ethylenediamine mono-p-toluenesulphonate are heated in 30 ml of isopentanol under boiling for 10 hours. After the solvent is distilled off, the residue is mixed with an aqueous solution of sodium carbonate. The separated sediment is filtered, washed with water and dried. 1.4 g (61% of the theoretical yield) of 2-(2',6'-dichlorophenylamino)-imidazoline-(2) with a melting point of 138°–141° are obtained.

EXAMPLE 20

2-(2',6'-dichlorophenylamino)-imidazoline-(2) hydrochloride 3.4 g (0.01 M) of N-(2,6-dichlorophenyl)-N'-benzoyl-S-methylisothiourea and 7.0 g (0.03 M) of ethylenediamine mono-p-toluenesulphonate are heated under boiling in 40 ml of n-amyl alcohol for 15 hours. The reaction mixture is washed twice with 50 ml of water. The solvent is distilled off. The residue is washed twice with 20 ml of a saturated aqueous solution of sodium carbonate, each time. To the washed residue is added hydrochloric acid (15% aqueous solution). The precipitate is dissolved by gentle heating. The obtained solution is subjected to vacuum distillation until dryness. The product is washed with acetone and is filtered. After drying 0.9 g of 2-(2',6'-dichlorophenylamino)-imidazoline-(2) hydrochloride are obtained.

EXAMPLE 21

2-(2',6'-dichlorophenylamino)-imidazoline-(2) hydrochloride 2.9 g (0.01 M) of N-(2,6-dichlorophenyl)-N'-propionyl)-S-methylisothiourea and 7.0 g (0.03 M) of ethylenediamine mono-p-toluene sulphonate are heated under boiling with 40 ml of n-amyl-alcohol for 75 hours. The reaction mixture is treated as in example 20. 1.2 g of 2-(2',6'-dichlorophenylamino)-imidzoline-(2) hydrochloride are isolated.

EXAMPLE 22

2-(2',5'-dichlorophenylamino)-imidazoline-(2)

2.8 g (0.01 M) of N-(2,5-dichlorophenyl)-N'-acetyl-S-methylisothiourea and 7.0 g (0.03 M) of ethylenediamine mono-p-toluenesulphonate are boiled with 30 ml of n-amyl alcohol for 5 hours. The reaction solution is washed with 50 ml of a saturated solution of sodium carbonate and 50 ml of water. The amyl alcohol is distilled off under vacuum until a dry residue is obtained which after being recrystallized from ethylacetate gives 1.5 g (65% of the theoretical yield of 2-(2',5'-dichlorophenylamino)-imidazoline (2) with a melting point of 179°–182° C. The hydroiodide salt of the above compound has a melting point of 275°–277° C. According to the U.S. Pat. No. 2,899,426 the melting point of 2-(2',5'-dichlorophenylamino)-imidazoline-(2) hydroiodide is 275.4°–277°.

EXAMPLE 23

2-(o-nitrophenylamino)-imidazoline-(2)

2.5 g (0.01 M) of N-(o-nitrophenyl)-N'-acetyl-S-methylisothiourea and 7.0 g (0.03 M) of ethylenediamine mono-p-toluene-sulphonate are boiled with 30 ml of n-amyl alcohol for 6 hours. The solution is washed with 50 ml of a saturated water solution of sodium carbonate and 50 ml water. The amyl alcohol is distilled off under vacuum. The residue is recrystallized from ethanol. 0.8 g (38% of the theoretical yield) of 2-(o-nitrophenylamino)-imidazoline-(2) are obtained with a melting point of 162°–166°.

According to the Bulgarian Patent Application No. 26251 the melting point of 2-(o-nitrophenylamino)-imidazoline-(2) is 165°–169°.

We claim:

1. A compound selected from the group consisting of:
   (a) N-(2,6-dichlorophenyl)-N'-acetyl-S-methyl-isothiourea;
   (b) N-(2,6-dichlorophenyl)-N'-acetyl-S-ethylosothiourea;
   (c) N-(2,6-dichlorophenyl)-N'-benzoyl-S-methylisothiourea;
   (d) N-(2,6-dichlorophenyl)-N'-propionyl-S-methyl-isothiourea;
   (e) N-(2,6-dichlorophenyl)-N'-acetyl-S-benzyl-isothiourea;
   (f) N-(2,6-dichlorophenyl)-N'-acetyl-S-n-butylisothiourea;
   (g) N-(2,5-dichlorophenyl)-N'-acetyl-S-methyl-isothiourea;
   (h) N-(3-iodophenyl)-N'-acetyl-S-methyl-isothiourea;
   (i) N-(o-fluorophenyl)-N'-benzoyl-S-ethylisothiourea;
   (j) N-(o-nitrophenyl)-N'-acetyl-S-methyl-isothiourea; and
   (k) N-(2,6-dichlorophenyl)-N'-acetyl-S-isobutylisothiourea.

2. N-(2,6-dichlorophenyl)-N'-acetyl-S-methyl-isothiourea.

* * * * *